United States Patent [19]

Haase et al.

[11] 4,247,476

[45] Jan. 27, 1981

[54] POLYMERIC QUATERNARY AMMONIUM SALTS CONTAINING SPECIFIC CATIONIC RECURRING UNITS

[75] Inventors: Jaroslav Haase, Riehen, Switzerland; Ulrich Horn, Greenville, S.C.; Hans-Ulrich Berendt, Allschwil, Switzerland

[73] Assignee: Ciba-Geigy Corporation, Ardsley, N.Y.

[21] Appl. No.: 911,725

[22] Filed: Jun. 1, 1978

[30] Foreign Application Priority Data

Jun. 10, 1977 [CH] Switzerland .................. 7178/77

[51] Int. Cl.³ .................. C07C 101/26; C07C 101/68; C07C 103/54; C07C 127/15
[52] U.S. Cl. .......................... 564/51; 8/639; 564/59; 548/341; 8/927; 549/76; 549/78; 564/156; 549/79; 560/76; 210/729; 560/84; 560/85; 252/8.6; 560/88; 252/8.8; 260/31.8 XA; 260/32.6 N; 260/32.6 NA; 260/32.6 NR; 260/347.3; 260/347.4; 260/456 P; 260/459 A; 260/464; 260/465 D; 260/465.4; 260/29.2 N; 528/422; 528/423; 564/157; 564/160; 424/327; 528/397; 544/59; 544/162; 544/163; 544/168; 546/174; 546/175; 546/186
[58] Field of Search .......... 260/553 R, 553 A, 558 A, 260/561 A, 561 R, 562 N, 562 R, 562 P, 459 A, 456 P, 32.4, 32.6 N, 32.6 NR, 32.6 NA, 31.8 XA, 31.8 U, 464, 465.4; 542/418; 528/52, 64, 61, 71, 288, 291, 292, 332, 422; 546/186; 560/76, 84, 85, 88

[56] References Cited

U.S. PATENT DOCUMENTS

| 2,375,853 | 5/1945 | Kirby et al. | 260/583 |
| 2,388,614 | 11/1945 | Kirby et al. | 260/583 X |
| 2,850,529 | 9/1958 | Pinson | 260/553 R |
| 2,926,119 | 2/1960 | Niederhauser | 260/558 A X |
| 2,940,851 | 6/1960 | Beavers et al. | 260/562 N X |
| 2,984,539 | 5/1961 | Matter et al. | 260/561 A X |
| 3,009,761 | 11/1961 | Taube et al. | 8/74 |
| 3,170,901 | 2/1965 | Melamed et al. | 260/561 A X |
| 3,715,335 | 2/1973 | Backsai | 528/288 |
| 3,778,476 | 12/1973 | Rembaum et al. | 528/61 X |
| 3,825,511 | 7/1974 | Markhart et al. | 528/422 X |
| 4,075,136 | 2/1978 | Schaper | 528/422 X |

FOREIGN PATENT DOCUMENTS

| 1379080 | 1/1975 | United Kingdom | 528/422 |
| 1410581 | 10/1975 | United Kingdom | 528/422 |
| 1479786 | 7/1977 | United Kingdom | 528/422 |
| 1486396 | 9/1977 | United Kingdom | 528/422 |
| 1513671 | 6/1978 | United Kingdom | 528/422 |

OTHER PUBLICATIONS

Rembaum et al., J. Phys. Chem., vol. 73, pp. 513-519 (1969).
Zipursky et al., J. Physiol. Pharmacol., vol. 43, pp. 289-297 (1965).

Primary Examiner—Floyd D. Higel
Attorney, Agent, or Firm—Edward McC. Roberts; Probodh I. Almaula; Michael W. Glynn

[57] ABSTRACT

Disclosed are novel polymeric quaternary ammonium salts containing specific di-tertiary amino substituted cationic recurring units. Said salts are useful as dyeing and finishing agents, especially for dyeing textile materials, such as polyacrylonitrile fiber materials, as dispersing agents and emulsifiers, as antistatic, antimicrobial and flocculating agents and as precipitants.

15 Claims, No Drawings

POLYMERIC QUATERNARY AMMONIUM SALTS CONTAINING SPECIFIC CATIONIC RECURRING UNITS

The present invention relates to novel polymeric quaternary ammonium salts, processes for their preparation and their use.

Polymeric quaternary ammonium salts and their use as bactericides are already known from U.S. Pat. No. 2,271,378. As a rule, they are obtained by reacting ditertiary amines with dihalides. Polymeric quaternary ammonium salts, as sensitisers in photographic materials, are described in British Patent Specification No. 1,169,896, whilst British Patent Specification 1,479,786 discloses polymeric quaternary ammonium salts which carry chemically reactive substituents on the quaternary nitrogen atoms. Finally, polymeric quaternary ammonium salts which are prepared using 4,4'-bis-(halogenomethyl)-diphenyls as the dihalides and which are used in particular as textile assistants are known from Belgian Patent Specification No. 849,728.

These known polymers are not yet able to meet all of the demands made on them (for example as textile assistants), so that the problem was to propose novel polymeric quaternary ammonium salts which have different and better characteristics and are thus better suited to the indicated purpose and in some cases also to other applications and to provide these salts according to the invention. In contrast to the known polymeric ammonium salts, other diamines and/or dihalides, or other combinations of diamines and dihalides, are used for the preparation of the polymeric quaternary ammonium salts according to the invention, the cationic recurring units of which are indicated in the formulae (1) and (2) given below, and these starting materials result in the products which have the surprisingly improved characteristics.

The present invention relates to polymeric quaternary ammonium salts which contain cationic units of the formula

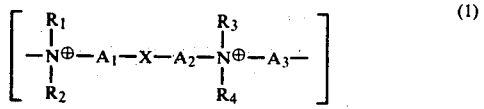

which can be combined with cationic units of the formula

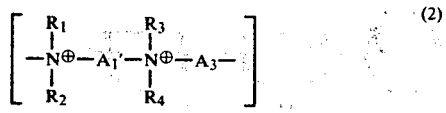

in which formulae $R_1$, $R_2$, $R_3$ and $R_4$ are identical or different from one another and are substituted or unsubstituted alkyl, cycloalkyl or alkenyl having at most 20 carbon atoms, aryl or aralkyl, or ($R_1$ and $R_2$) and/or ($R_3$ and $R_4$), together with the nitrogen atom to which they are bonded, form a substituted or unsubstituted heterocyclic ring having 5 or 6 ring members, $A_1$ and $A_2$ are —$C_nH_{2n}$—, in which n is 1 to 12 and the sum of n in $A_1$ and $A_2$ is at least 3, and when n is 1 the bond to the bridge member X is not via a nitrogen or oxygen atom, or are phenylene which is unsubstituted or substituted by halogen, hydroxyl, alkyl, halogenoalkyl or alkoxy, and $A_1$ and $A_2$ are identical or different from one another, $A'_1$ is —$C_nH_{2n}$—, in which n is 2 to 12, $A_3$ is —$C_mH_{2m}$—, —$CH_2O$—$R_5$—$OCH_2$—, —$CH_2(OR_6)_pOCH_2$—, —$CH_2COCH_2$—, —$CH_2CHOHCH_2$—,

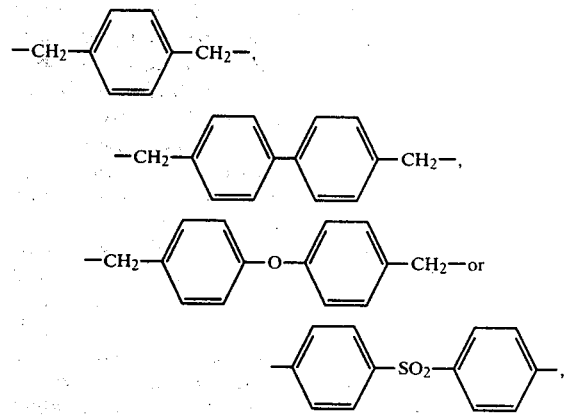

in which $R_5$ is straight-chain or branched alkylene having 2 to 12 carbon atoms, which is unsubstituted or substituted by halogen, $R_6$ is —$CH_2CH_2$—,

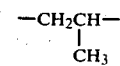

or —$(CH_2)_4$—, m is 2 to 12 and p is 2 to 15, and X is a divalent bridge member of the formula —NHCONH—, —NHCOX$_1$CONH—, —CONH—, OCONH—, —COO—, —COX$_2$CO—,

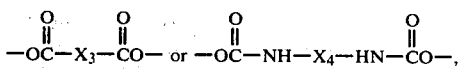

in which $X_1$ is a direct bond, alkylene, alkenylene, arylene, diaminoalkylene, diaminoarylene, dioxyalkylene, polyoxyalkylene or dioxyarylene, $X_2$ is diaminoalkylene, dioxyalkylene, polyoxyalkylene or dithioalkylene, $X_3$ is arylene and $X_4$ is alkylene or arylene.

The present invention also relates to processes for the preparation of the novel polymeric quaternary ammonium salts, their use, methods of application in which the polymeric quaternary ammonium salts are employed and also the compositions of carrying out these methods.

The radicals $R_1$, $R_2$, $R_3$ and $R_4$ in the cationic units, of the polymeric quaternary ammonium salts, of the formulae (1) and (2) can be straight-chain or branched alkyl radicals having 1 to 20 carbon atoms, for example methyl, ethyl, propyl, isopropyl, butyl, isobutyl, tert.-butyl, hexyl, octyl, isooctyl, tert.-octyl, decyl, dodecyl, tetradecyl, hexadecyl, octadecyl or eicosyl.

Alkyl radicals having 1 to 10 and especially having 1 to 4 carbon atoms are preferred; methyl and ethyl are particularly suitable.

Substituted alkyl radicals are, for example, hydroxyalkyl, cyanoalkyl, alkoxyalkyl, alkylthioalkyl, alkylcarbonylalkyl, alkylsulphonylalkyl, arylcarbonylalkyl and arylsulphonylalkyl, in which aryl is a mono-, di- or tri-nuclear aromatic hydrocarbon, especially phenyl or naphthyl; alkylcarboxylic acid, carbalkoxyalkyl and dicarbalkoxyalkyl; and carboxylic acid amide-alkyl, which is unsubstituted of N- or N,N-substituted by lower alkyl ($C_1$–$C_4$) or aryl, for example phenyl.

The cycloalkyl radicals are essentially cyclopentyl and cyclohexyl, which can be substituted.

The alkenyl radicals can contain 2 to 20 carbon atoms. Preferred radicals are those having 2 to 10 or especially 2 to 4 carbon atoms. The alkenyl radicals which correspond to the said alkyl radicals are suitable. The substituents mentioned for the alkyl radicals can generally also be used for the alkenyl radicals.

Aryl and aralkyl radicals are in particular phenyl and benzyl, which are unsubstituted or substituted by hydroxyl, cyano, halogen (fluorine, chlorine, bromine or iodine) or carboxyl; alkyl, hydroxyalkyl, cyanoalkyl, alkoxy and alkylthio, lower alkyl and alkoxy radicals being preferred; alkoxyalkyl, carbalkoxyalkyl and dicarbalkoxyalkyl, the alkyl and alkoxy moiety in each case preferably containing 1 to 4 carbon atoms; alkylcarboxylic acid, in which alkyl preferably contains 1 to 4 carbon atoms; or carboxylic acid amide-alkyl, which is unsubstituted or N- or N,N-substituted by lower alkyl ($C_1$–$C_4$).

The two substituents on each nitrogen can also, together with the nitrogen atom to which they are bonded, form a substituted or unsubstituted heterocyclic ring having 5 or 6 ring members. Examples of such hetercyclic rings are the piperidine, morpholine, thiomorpholine, pyrrolidine or imidazoline ring.

$A_1$ and $A_2$, which can be identical or different from one another, are, for example, the alkylene grouping of the formula —$C_nH_{2n}$—, in which n is an integer from 1 to 12 and preferably 1 to 6. When n is 1, i.e. in the case of the —$CH_2$— grouping, the bond to the bridge member X must be effected via atoms other than nitrogen and oxygen; in particular, the bond is effected via a carbon atom. Furthermore, the sum of n in the two —$C_nH_{2n}$— groups of $A_1$ and $A_2$ must be at least 3. As already indicated by the formula —$C_nH_{2n}$—, the alkylene radicals can be branched or straight-chain, the latter being preferred.

$A_1$ and $A_2$ can also be an aromatic bridge member, especially a substituted or unsubstituted phenylene.

Possible substituents on these aromatic bridge members are as a rule lower alkyl, lower hydroxy- or halogeno-alkyl having 1 to 4 carbon atoms, hydroxyl and halogen, especially chlorine or bromine.

$A'_1$ can be branched, but especially straight-chain, alkylene having 2 to 12 carbon atoms, for example —$(CH_2)_2$—, —$(CH_2)_3$—, —$(CH_2)_6$—or —$(CH_2)_{12}$—.

The radical $A_3$ is alkylene and can be represented by the formula —$C_mH_{2m}$—, in which m is 2 to 12. Individual groupings are those which follow: —$C_2H_4$—, —$C_3H_6$—, —$C_4H_8$—, —$C_5H_{10}$—, —$C_6H_{12}$—, —$C_8H_{16}$—, —$C_{10}H_{20}$— and $C_{12}H_{24}$—. These groupings can be straight-chain or branched. $A_3$ is also —$CH_2O$—$R_5$—$OCH_2$—, in which $R_5$ is straight-chain or branched alkylene having 2 to 12 carbon atoms; the alkylene groups here are, in particular, again the abovementioned groupings, which can be substituted by halogen, preferably chlorine or bromine.

$A_3$ is also —$CH_2(OR_6)_pOCH_2$—, in which $R_6$ is —$CH_2CH_2$—,

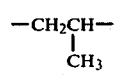

or —$(CH_2)_4$— and p is 2 to 15, or the following groups: —$CH_2COCH_2$—, —$CH_2CHOHCH_2$—,

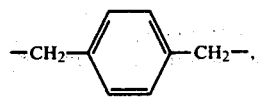

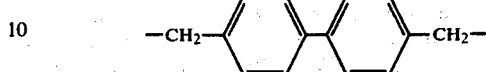

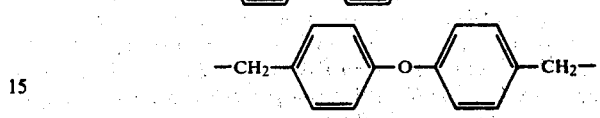

(except for for the p,p'-isomers, other isomers can also be used) or

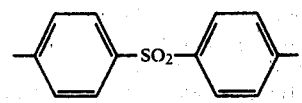

The bridge member X comprises divalent radicals of the formulae —NHCONH—, —NHCOX$_1$CONH—, —CONH—, —OCONH—, —COO—, —COX$_2$CO—,

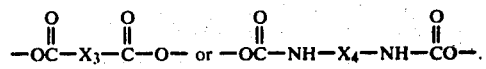

$X_1$ is a direct bond and also alkylene, for example having 1 to 12 carbon atoms. In addition to methylene (—$CH_2$—), such groupings are, in particular, those already mentioned for $A_3$ and these can be straight-chain or branched. If $X_1$ is alkenylene, it can be represented, for example, by the formulae —CH═CH— or —CH═CH—CH═CH— and also

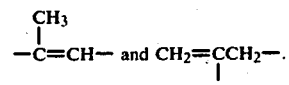

Aromatic bridge members ($X_1$=arylene) are, for example, those of the formulae

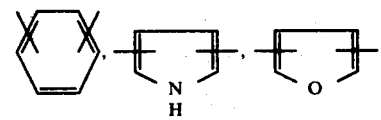

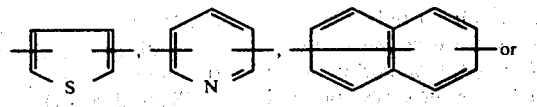

in which the aromatic rings can be substituted by halogen, especially chlorine or bromine, alkyl and/or alkoxy.

The alkyl and alkoxy radicals as a rule contain 1 to 5 carbon atoms and are, for example, methyl, ethyl, propyl, isopropyl, butyl, isobutyl, tert.-butyl, amyl or isoamyl; and also methoxy, ethoxy, propoxy, butoxy or pentoxy and the corresponding branched-chain isomers. The aromatic rings can contain one or more substituents. $X_1$ is also diaminoalkylene, for example of the formula —NH—$C_mH_{2m}$—NH— or especially —NH$(CH_2)_m$NH—, in which m is an integer from 2 to 12. The alkylene groupings already mentioned when defining $A_3$ are preferred. The diaminoarylene radicals are preferably those of the formula

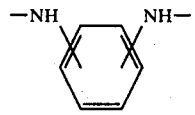

and especially of the formula

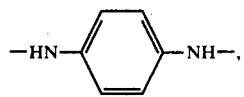

in which the phenyl nucleus can be substituted by halogen, especially chlorine or bromine, alkyl, especially having 1 to 5 carbon atoms, or alkoxy, especially having 1 to 4 carbon atoms, and one or more substituents can be present on the phenyl nucleus. The dioxy- and polyoxyalkylene radicals, which can be present as bridge members $X_1$, can be represented by the formulae —O$R_5$O— and —$(OR_6)_pO$—, in which $R_5$, $R_6$ and p are as defined. Examples of dioxyalkylene radicals are —O$(CH_2)_2$O— or —O$(CH_2)_4$O— and of polyoxyalkylene radicals are —OCH$_2$CH$_2$OCH$_2$CH$_2$O—, —(OCH$_2$CH$_2$)$_{15}$O—,

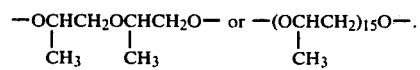

The dioxyarylene radicals can have the formula

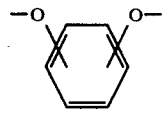

and especially the formula

in which the phenyl nucleus can be substituted by halogen, especially chlorine or bromine, alkyl, especially having 1 to 5 carbon atoms, or alkoxy, especially having 1 to 4 carbon atoms, and one or more substituents can be present on the phenyl nucleus. Furthermore, the radical of the formula

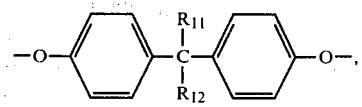

in which $R_{11}$ and $R_{12}$ are hydrogen or methyl, is also suitable. The bridge member $X_2$ within the grouping —CO$X_2$CO— is diaminoalkylene, dioxyalkylene or polyoxyalkylene and can have the meanings defined above for the same groupings for $X_1$. If $X_2$ is dithioalkylene, these radicals can preferably be represented by the formula —S$R_5$S—, in which $R_5$ is as defined.

$X_3$ is arylene and can be, in particular, phenylene, and the phenyl ring can contain halogen or lower alkyl, for example having 1 to 4 carbon atoms, as substituents. $X_4$ is alkylene, especially straight-chain alkylene having 1 to 12 and preferably 2 to 6 carbon atoms. If $X_4$ is arylene, it has, in particular, the meanings defined for $X_3$.

The polymeric quaternary ammonium salts according to the invention contain cationic units of the formula (1) which can be combined with the cationic units of the formula (2), i.e., for example,

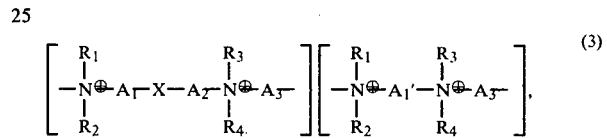

and these units can, for example, be arranged in the molecule in an alternating manner and/or as blocks.

Preferred polymeric quaternary ammonium salts are those which contain only recurring units of the formula (1), in which the bridge member X is in particular —NHCONH—, —NHCOX$_1$CONH—, —CONH—, —OCONH—, —COO— or —COX$_2$CO—, X$_1$ is alkylene, alkenylene, arylene, diaminoalkylene, diaminoarylene, dioxyalkylene, polyoxyalkylene or dioxyarylene and X$_2$ is diaminoalkylene, dioxyalkylene, polyoxyalkylene or dithioalkylene.

Particularly suitable polymeric quaternary ammonium salts of the formula (1) contain cationic units of the formula

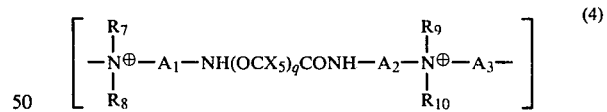

in which $R_7$, $R_8$, $R_9$ and $R_{10}$ are identical or different from one another and are cycloalkyl having 5 to 6 carbon atoms; alkyl, hydroxyalkyl, cyanoalkyl, alkoxyalkyl, alkylthioalkyl and alkylcarbonylalkyl having 1 to 10 carbon atoms; arylcarbonylalkyl, alkylsulphonylalkyl and arylsulphonylalkyl each having 1 to 4 carbon atoms in the alkyl moiety; alkylcarboxylic acid having 1 to 4 carbon atoms in the alkyl moiety; carbalkoxyalkyl and di-(carbalkoxy)-alkyl each having 1 to 4 carbon atoms in the alkoxy moiety and in the alkyl moiety; carboxylic acid amide-alkyl which has 1 to 10 carbon atoms in the alkyl moiety and is unsubstituted or N-substituted by lower alkyl or aryl; or phenyl or benzyl, which are unsubstituted or substituted by hydroxyl, cyano, halogen and carboxyl; alkyl, hydroxyalkyl, cyanoalkyl, alkoxy and alkylthio having 1 to 4 carbon atoms; alkoxyalkyl, carbalkoxyalkyl and di-(carbalkoxy)-alkyl each having 1 to 4 carbon atoms in the alkyl moiety and in the alkoxy moiety; alkylcarboxylic acid having 1 to 4 carbon atoms in the alkyl moiety or carboxylic acid amide-alkyl which has 1 to 4 carbon atoms in the alkyl moiety and is unsubstituted or N-substituted by lower alkyl; or ($R_7$ and $R_8$) and/or ($R_9$ and $R_{10}$), together with the nitrogen atom to which they are bonded, form a substituted or unsubstituted heterocyclic ring having 5 or 6 ring members, $X_5$ is —$C_rH_{2r}$—, in which r is an integer from 1 to 12, —(CH=CH—)$_s$, in which s is 1 or 2,

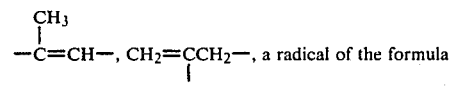, a radical of the formula

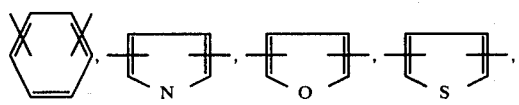

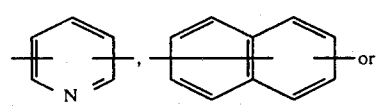

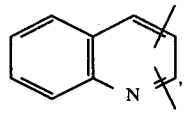

in which the aromatic rings can be substituted by halogen, alkyl and/or alkoxy, —NH(CH$_2$)$_m$NH—, in which m is 2 to 12,

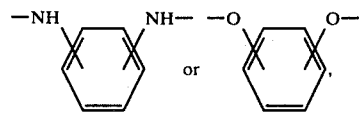

in which the phenylene ring can be substituted by halogen, alkyl and/or alkoxy,

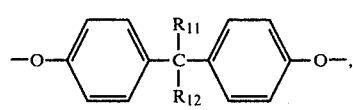

in which $R_{11}$ and $R_{12}$ are hydrogen or methyl, —OR$_5$O— or —(OR$_6$)$_p$O—, in which $R_5$, $R_6$, p and $A_1$, $A_2$ and $A_3$ are as defined and q is 0 or 1. Further interesting compounds are those containing recurring units of the formula (4) in which $X_5$ is a direct chemical bond and q is 1 and which preferably contain recurring units of the formula

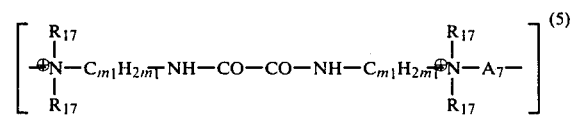 (5)

in which $R_{17}$ is alkyl having 1 to 4 carbon atoms, $A_7$ is —$C_mH_{2m}$—,

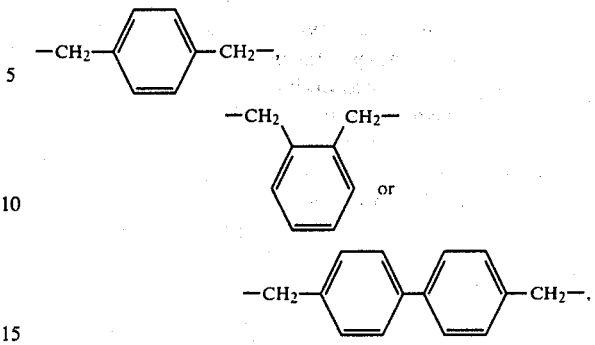

m is 2 to 12 and m$_1$ is 2 to 6.

Further preferred compounds are the polymeric quaternary ammonium salts in which the cationic units are of the formula

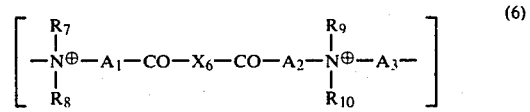 (6)

in which $X_6$ is —OR$_5$O—, —(OR$_6$)$_p$O—, —S(CH$_2$)$_m$S— or —HN(CH$_2$)$_m$NH— and $R_5$, $R_6$, m, p, $A_1$, $A_2$, $A_3$, $R_7$, $R_8$, $R_9$ and $R_{10}$ are as defined, or in which the cationic units are of the formula

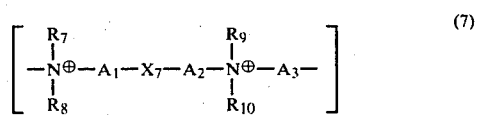 (7)

in which $X_7$ is —CONH—, —OCONH— or —COO— and $A_1$, $A_2$, $A_3$ and $R_7$, $R_8$, $R_9$ and $R_{10}$ are as defined. Particularly suitable representatives containing recurring units of the formula (7) are those in which the cationic units are of the formula

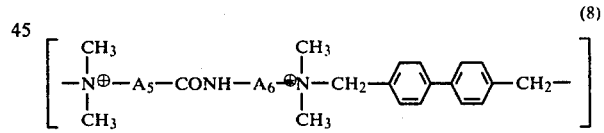 (8)

in which $A_5$ is alkylene having 1 to 4 carbon atoms or phenylene and $A_6$ is alkylene having 2 to 6 carbon atoms or phenylene.

A further group of very suitable polymeric quaternary ammonium salts of the formula (1) contains cationic units of the formula

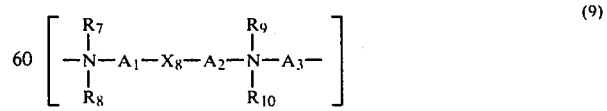 (9)

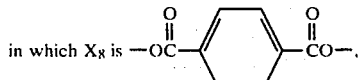

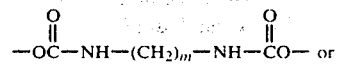 or

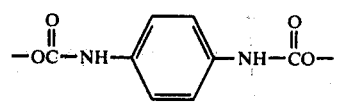

and m is 2 to 12 and $A_1$, $A_2$, $A_3$, $R_7$, $R_8$, $R_9$ and $R_{10}$ are as defined.

Very particularly advantageous salts are, moreover, the polymeric quaternary ammonium salts in which the cationic units are of the formula

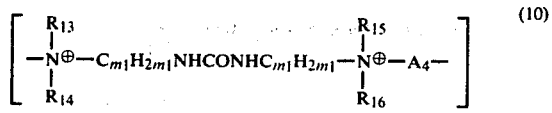

in which $R_{13}$, $R_{14}$, $R_{15}$ and $R_{16}$ are identical or different from one another and are alkyl, hydroxyalkyl, alkoxyalkyl, alkylthioalkyl and cyanoalkyl having 1 to 4 carbon atoms, cyclopentyl, cyclohexyl, $CH_3COCH_2-$, $H_2NCOCH_2-$ or

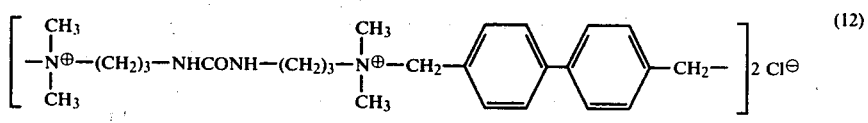

or phenyl or benzyl, which are unsubstituted or substituted by hydroxyl, cyano, fluorine, chlorine, bromine, alkyl, hydroxyalkyl, cyanoalkyl, alkoxy and alkylthio having 1 or 2 carbon atoms, alkoxyalkyl, carbalkoxyalkyl and di-(carbalkoxy)-alkyl each having 1 or 2 carbon atoms in the alkyl moiety and in the alkoxy moiety, $-CH_2COOH$, $-(CH_2)_2COOH$, or carboxylic acid amide-alkyl which has 1 or 2 carbon atoms in the alkyl moiety and is unsubstituted or N-substituted by lower alkyl; or ($R_{13}$ and $R_{14}$) and/or ($R_{15}$ and $R_{16}$), together with the nitrogen atom to which they are bonded, form a heterocyclic ring of the formula

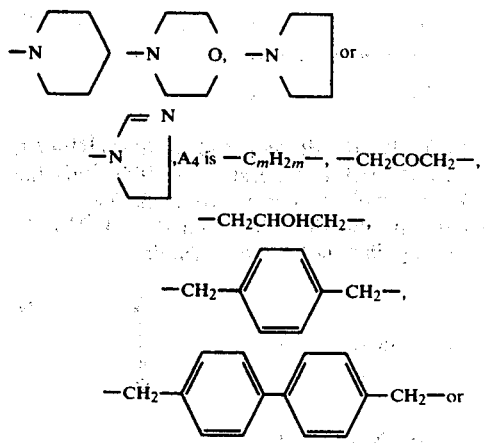

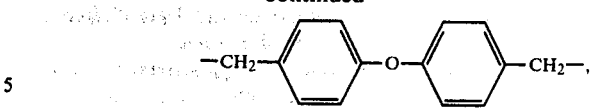

m is 2 to 12 and $m_1$ is 2 to 6.

Particularly preferred compounds are, now, those containing recurring units of the formula (10) in which $R_{13}$, $R_{14}$, $R_{15}$ and $R_{16}$ are identical or different from one another and are alkyl having 1 to 4 carbon atoms, or ($R_{13}$ and $R_{14}$) and ($R_{15}$ and $R_{16}$), together with the nitrogen atom to which they are bonded, form a piperidine ring, and $A_4$, m and $m_1$ are as defined, and in which the cationic units are of the formula

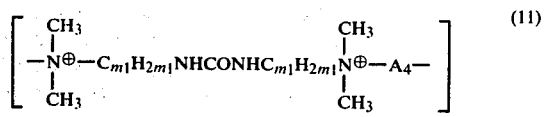

in which $A_4$ and $m_1$ are as defined, or of the formula

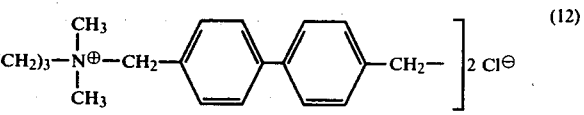

Particularly preferred polymeric quaternary ammonium salts containing recurring units of the formula (1) are those in which $R_1$, $R_2$, $R_3$ and $R_4$ are identical or different from one another and are methyl or ethyl, or ($R_1$ and $R_2$) and ($R_3$ and $R_4$), together with the nitrogen atom to which they are bonded, form a piperidine ring, $A_1$ and $A_2$ are $-(CH_2)_n-$, in which $n_1$ is 1 to 3 and the sum of $n_1$ in $A_1$ and $A_2$ is at least 3, or are phenylene, $A_3$ is $-C_mH_{2m}-$, $-CH_2O(CH_2)_{n2}OCH_2-$, $-CH_2COCH_2-$, $CH_2CHOHCH_2-$,

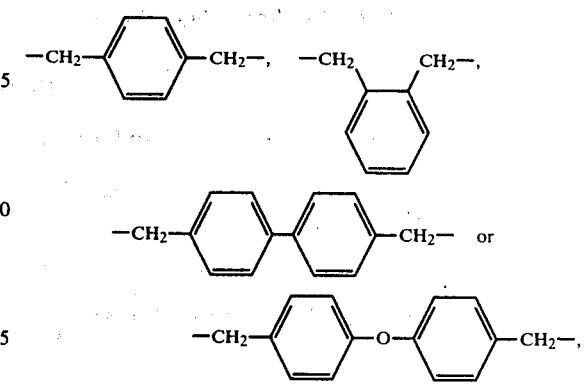

m is 2 to 12, $n_2$ is 2 to 6 and X is a divalent bridge member of the formula $-NHCONH-$, $-NHCOX_1$-$CONH-$, $-CONH-$, $-COX_2CO-$,

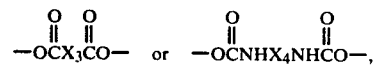

in which $X_1$ is a direct bond, alkylene having 1 to 6 carbon atoms, phenylene, diaminoalkylene having 1 to 6 carbon atoms or diaminophenylene and the phenylene ring can be substituted by methyl, $X_2$ is
—$NH(CH_2)_{n2}NH$—, $X_3$ is phenylene and $X_4$ is alkylene
having 2 to 6 carbon atoms or phenylene.

Suitable anions for the polymeric quaternary ammonium salts according to the invention are all conventional inorganic or organic anions which do not form sparingly soluble complexes with the cations, since the ammonium salts should preferably be soluble in water. Examples are the anions of the mineral acids or of low-molecular weight organic acids. Suitable anions are, for example, the halogen anions, such as $I^\ominus$, $Br^\ominus$ and especially $Cl^\ominus$, methyl-sulphate ($CH_3SO_4^\ominus$), ethyl-sulphate ($C_2H_5SO_4^\ominus$), toluenesulphonate, nitrate and sulphate.

The polymeric quaternary ammonium salts according to the invention can have molecular weights of 1,000 to 100,000, preferably of 2,000 to 50,000 and especially of about 4,000 to about 20,000. They are soluble in water.

The ammonium salts can be prepared in accordance with known methods, by, for example, reacting diamines (mixtures of diamines) with corresponding dihalogen compounds (mixtures of compounds) in molar ratios of about 1:2 to 2:1 and preferably in equimolar amounts.

Thus, the compounds containing recurring units of the formula (1) and optionally (2) can be obtained by reacting diamines of the formula

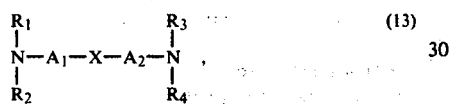

optionally as a mixture with diamines of the formula

in which formulae $R_1$, $R_2$, $R_3$, $R_4$, $A_1$, $A_2$, $A'_1$ and $X$ are as defined, with dihalides or optionally mixtures of dihalides, of the formula $$X_9—A_3—X_9 \qquad (15)$$

in which $X_9$ is halogen, especially chlorine or bromine, and $A_3$ is as defined.

A further possibility can also comprise reacting dihalides of the formula $$X_9—A_1—X—A_2—X_9 \qquad (16)$$

optionally as a mixture with dihalides of the formula
$$X_9—A'_1—X_9, \qquad (17)$$

in which formulae $A_1$, $A_2$, $A'_1$ and $X$ and $X_9$ are as defined, with diamines of the formula

in which $R_1$, $R_2$, $R_3$, $R_4$ and $A_3$ are as defined.

In order to obtain the particularly suitable ammonium salts containing the recurring units of the formula (4), diamines of the formula

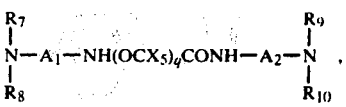

in which $R_7$, $R_8$, $R_9$, $R_{10}$, $A_1$, $A_2$, $X_5$ and $q$ are as defined, can, for example, be employed; in order to obtain the ammonium salts containing the recurring units of the formula (5), the amines of the formula

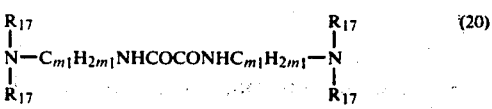

and the dihalides of the formula
$$X_9—A_7—X_9, \qquad (21)$$

in which formulae $R_{17}$, $A_7$, $X_9$ and $m_1$ are as defined, can be employed; and in order to obtain the ammonium salts containing the recurring units of the formulae (6) and (7), the diamines of the formulae

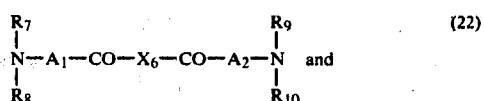

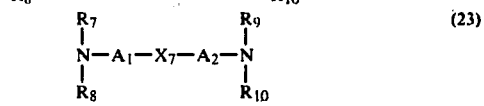

in which $R_7$, $R_8$, $R_9$, $R_{10}$, $A_1$, $A_2$, $X_6$ and $X_7$ are as defined, can be employed.

The ammonium salts containing the recurring units of the formula (8) are prepared, for example, by reacting the diamines of the formula

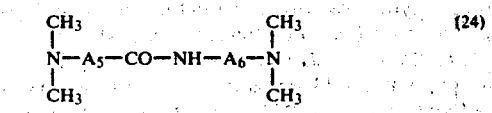

in which $A_5$ and $A_6$ are as defined, with 4,4'-bis-(chloromethyl)-diphenyl.

In order to prepare the ammonium salts containing the recurring units of the formula (9), the diamines of the formula

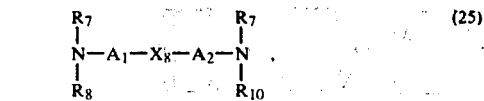

in which $A_1$, $A_2$, $R_7$, $R_8$, $R_9$, $R_{10}$ and $X_8$ are as defined, can be reacted with dihalides of the formula $X_6—A_3—X_6$, in which $X_6$ and $A_3$ are as defined.

The ammonium salts of the formula (10) can be prepared by reacting diamines of the formula

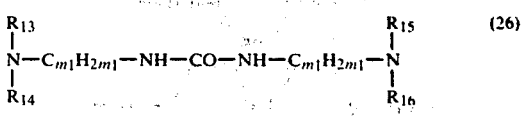

with dihalides of the formula $$X_6-A_4-X_6,$$

in which formulae $R_{13}$, $R_{14}$, $R_{15}$, $R_{16}$, $A_4$, $X_6$ and $m_1$ are as defined. In particular, $R_{13}$, $R_{14}$, $R_{15}$ and $R_{16}$ are identical or different from one another and are alkyl having 1 to 4 carbon atoms, preferably methyl, or ($R_{13}$ and $R_{14}$) and ($R_{15}$ and $R_{16}$), together with the nitrogen atom to which they are bonded, form a piperidine ring, whilst $A_4$ is as defined and $m_1$ is 2 to 6, preferably 3.

The starting compounds (diamines and dihalides) for the preparation of the polymeric quaternary ammonium salts according to the invention are in general known compounds which are readily accessible by chemical synthesis.

Dihalides of the formula (27) are, for example, $Br(CH_2)_6Br$, $Br(CH_2)_{10}Br$, $Br(CH_2)_{12}Br$, $ClCH_2COCH_2Cl$,

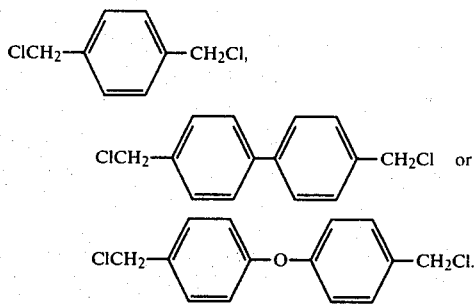

The aromatic dihalides can be obtained easily, for example by chloromethylation. Diamines containing the urea bridge member (—HNCONH—) and an alkylene bridge member to the tertiary nitrogen atoms can be obtained by reacting urea with alkylenediamines which contain a tertiary nitrogen atom, at relatively high temperatures, with the elimination of ammonia. Another possibility for the preparation of the diamines comprises reacting the corresponding α,ω-dihalogeno compounds with secondary amines. The diamines containing a bridge member which is derived from dicarboxylic acids can be prepared, for example, from the dichlorides or dialkyl esters of the acids and alkylenediamines. The preparation of the ammonium salts according to the invention can be carried out in solvents which are inert towards the reactants, for example alcohols, glycols, ketones, for example acetone, or cyclic ethers, such as dioxane or tetrahydrofurane. Preferred alcohols are the lower alcohols, especially methanol. The reaction temperature usually depends on the boiling points of the solvents used and can be about 20° to 150° C., preferably 50° to 100° C.

If desired, the reaction can also be carried out in water or water/alcohol mixtures as the solvent or in certain cases can also be carried out without a solvent.

As a result of the preferred combination of inexpensive and readily accessible dichlorine compounds for the preparation of the polymeric quaternary ammonium salts according to the invention, the salts preferably contain chlorine ions as the anions. The introduction of other anions can preferably be carried out by introducing other anions into the ammonium salts containing chlorine ions (the reaction products), for example by ion exchange.

The polymeric quaternary ammonium salts according to the invention are usually soluble in water and as a rule are obtained from the preparation in quantitative yield in the form of mixtures and not of pure compounds. The indicated molecular weight can therefore be regarded only as mean molecular weights.

The polymeric quaternary ammonium salts according to the invention can be employed for very diverse applications. The application baths can be neutral, acid or alkaline. A preferred application relates to a process for dyeing or printing textile materials of natural or synthetic fibres, in which the polymeric quaternary ammonium salts can be employed as dyeing assistants and especially as levelling agents. The textile materials made of natural fibres are those made of cellulose materials, especially those made of cotton and also of wool and silk, whilst the textile materials made of synthetic fibres are, for example, those made of high molecular weight polyesters, for example polyethylene terephthalate or polycyclohexanedimethylene terephthalate; polyamides, such as those made of polyhexamethylenediamine adipate, poly-ε-caprolactam or poly-ω-aminoundecanoic acid; polyolefins or polyacrylonitriles and also those made of polyurethanes, polyvinyl chlorides or polyvinyl acetates and also of cellulose 2½-acetate and cellulose triacetate. The said synthetic fibres can also be employed as mixtures with one another or as a mixture with natural fibres, such as cellulose fibres or wool.

These fibre materials can be in all states of processing suitable for a continuous operation, for example in the form of cable, slubbings, filaments, yarns, woven fabrics, knitted fabrics or nonwoven articles.

The dyeing preparations can be in the form of aqueous or aqueous-organic solutions or dispersions or in the form of printing pastes, which contain, in addition to a dye and the polymeric quaternary ammonium salts according to the invention, yet further additives, for example acids, salts, urea and further assistants, such as oxalkylation products of fatty amines, fatty alcohols, alkylphenols, fatty acids and fatty acid amides.

The polymeric quaternary ammonium salts are particularly suitable as retarders when dyeing polyacrylonitrile fibre materials with cationic dyes and in some cases also when dyeing anionically modified polyester fibre materials. They have an outstanding retarder and levelling capacity.

The cationic dyes which are used can belong to very diverse groups. Suitable dyes are, for example, diphenylmethane dyes, triphenylmethane dyes, rhodamine dyes and azo or anthraquinone dyes containing onium groups, and also thiazine, oxazine, methine and azomethine dyes.

The dyeing of the polyacrylonitrile textile materials can be carried out in a conventional manner by introducing the material to be dyed into an aqueous liquor which has been warmed to about 50° to 60° C. and contains the cationic dye, the polymeric quaternary ammonium salt, additives consisting of salts, such as sodium acetate and sodium sulphate, and also acids, such as acetic acid or formic acid, then raising the temperature of the dyebath to approximately 100° C. in the course of about 30 minutes and then keeping the dyebath at this temperature until it is exhausted. However, it is also possible to add the basic dye to the dyebath only at a later stage, for example when the temperature of the bath has risen to about 60° C. Furthermore, it is also possible to pretreat the material, to be dyed, at a temperature of 40° to 100° C. with a liquor which contains the conventional salts and acids as well as the polymeric ammonium salt but does not contain any dye and only then to add the dye and to carry out dyeing at 100° C.

Polyacrylonitrile fibre materials are also to be understood as meaning those materials which have been prepared using yet further vinyl compounds, for example vinyl chloride, vinyl acetate, vinylidene chloride, vinylidene cyanide and alkyl acrylates, in addition to acrylonitrile, if the proportion of these other vinyl compounds is not greater than 20%, based on the weight of the materials.

Advantageous amounts of polymeric quaternary ammonium salts which are employed in these dyeing methods are in general in the range of 0.01 to 5 percent by weight and especially of 0.05 to 2 or of 0.1 to 1 percent by weight, based on the weight of the fibre materials.

The dyeings produced on polyacrylonitrile fibres using the polymeric quaternary ammonium salts as assistants are distinguished by very good levelness and at the same time have a good dye yield on the fibre.

Further applications for the polymeric quaternary ammonium salts according to the invention are: reserving agents when dyeing polyacrylonitrile fibres; dispersing agents, for example for pigments; emulsifiers; cationic fixing agents for improving the wet fastness properties of cellulose textile fibre materials or paper dyed with direct and disperse dyes; antistatic agents, especially for textile materials containing synthetic organic fibres; antimicrobial agents; precipitants, for example when purifying waste water; or flocculating agents, for example for coagulating colloidal aqueous dispersions, for example dye dispersions.

The compounds can preferably be used as retarders when dyeing textile materials made of polyacrylonitrile fibres and in processes for fixing dyes; and also as antistatic agents and antimicrobial agents, and as precipitants and flocculating agents.

In the following examples the parts and percentages are by weight unless otherwise stated.

EXAMPLE 1

Equimolar amounts (0.2 mol in each case) of the dihalides indicated in Table 1 and of 1,3-bis-(3-dimethylaminopropyl)-urea (prepared from 1-dimethylamino-3-aminopropane and urea with the elimination of ammonia) are heated in 200 of methanol at the reflux temperature for 24 hours. In the course of the reaction, the viscosity of the reaction mixture gradually increases. After the reaction has ended, the reaction mixture is cooled and the solvent is removed in vacuo. Reaction products containing the recurring units indicated in Table 1 are obtained in quantitative yield (100% of theory).

The reaction products are soluble in water. Stable aqueous solutions contain, for example, 20 percent by weight of the reaction products.

The inherent viscosity (dl/g) is measured in methanol at a concentration of 0.5% (g/volume) at 25° C.

Table 1

| Dihalide | Reaction product containing recurring units of the formula | Content of ionic halogen in % of theory | Viscosity ($\mu$) |
|---|---|---|---|
| (a) ClCH$_2$—⟨phenyl⟩—⟨phenyl⟩—CH$_2$Cl | (101) $\left[-\underset{CH_3}{\overset{CH_3}{\underset{|}{\overset{|}{N^{\oplus}}}}}(CH_2)_3NHCONH(CH_2)_3-\underset{CH_3}{\overset{CH_3}{\underset{|}{\overset{|}{N^{\oplus}}}}}-CH_2-⟨phenyl⟩-⟨phenyl⟩-CH_2-\right]2Cl^{\ominus}$ | 91.3 | 2.20 |
| (b) ClCH$_2$—⟨phenyl⟩—CH$_2$Cl | (102) $\left[-\underset{CH_3}{\overset{CH_3}{\underset{|}{\overset{|}{N^{\oplus}}}}}(CH_2)_3NHCONH(CH_2)_3-\underset{CH_3}{\overset{CH_3}{\underset{|}{\overset{|}{N^{\oplus}}}}}-CH_2-⟨phenyl⟩-CH_2-\right]2Cl^{\ominus}$ | 92.2 | 0.52 |
| (c) ClCH$_2$COCH$_2$Cl | (103) $\left[-\underset{CH_3}{\overset{CH_3}{\underset{|}{\overset{|}{N^{\oplus}}}}}(CH_2)_3NHCONH(CH_2)_3-\underset{CH_3}{\overset{CH_3}{\underset{|}{\overset{|}{N^{\oplus}}}}}-CH_2COCH_2-\right]2Cl^{\ominus}$ | 97 | 0.24 |
| (d) Br(CH$_2$)$_6$Br | (104) $\left[-\underset{CH_3}{\overset{CH_3}{\underset{|}{\overset{|}{N^{\oplus}}}}}(CH_2)_3NHCONH(CH_2)_3-\underset{CH_3}{\overset{CH_3}{\underset{|}{\overset{|}{N^{\oplus}}}}}-(CH_2)_6-\right]2Br^{\ominus}$ | 94 | 0.34 |
| (e) Br(CH$_2$)$_{12}$Br | (105) $\left[-\underset{CH_3}{\overset{CH_3}{\underset{|}{\overset{|}{N^{\oplus}}}}}(CH_2)_3NHCONH(CH_2)_3-\underset{CH_3}{\overset{CH_3}{\underset{|}{\overset{|}{N^{\oplus}}}}}-(CH_2)_{12}-\right]2Br^{\ominus}$ | 93 | 0.56 |
| (f) Br(CH$_2$)$_{10}$Br | (106) $\left[-\underset{CH_3}{\overset{CH_3}{\underset{|}{\overset{|}{N^{\oplus}}}}}(CH_2)_3NHCONH(CH_2)_3-\underset{CH_3}{\overset{CH_3}{\underset{|}{\overset{|}{N^{\oplus}}}}}-(CH_2)_{10}-\right]2Br^{\ominus}$ | 94 | 0.38 |
| (g) BrCH$_2$CH$_2$Br | (107) $\left[-\underset{CH_3}{\overset{CH_3}{\underset{|}{\overset{|}{N^{\oplus}}}}}(CH_2)_3NHCONH(CH_2)_3N^{\oplus}CH_2CH_2-\right]2Br^{\ominus}$ | 91 | 0.22 |

Table 1-continued

| Dihalide | Reaction product containing recurring units of the formula | Content of ionic halogen in % of theory | Viscosity ($\mu$) |
|---|---|---|---|
| (h) BrCH$_2$—C$_6$H$_4$—CH$_2$Br (ortho) | (108) $\left[ -\overset{\oplus}{\underset{CH_3}{\underset{|}{N}}}(CH_3)(CH_2)_3NHCONH(CH_2)_3\overset{\oplus}{\underset{CH_3}{\underset{|}{N}}}(CH_3)CH_2{-}C_6H_4{-}CH_2{-} \right]$ 2Br$^\ominus$ | 98 | 0.17 |
| (i) ClCH$_2$—C$_6$H$_4$—O—C$_6$H$_4$—CH$_2$Cl | (109) $\left[ -\overset{\oplus}{\underset{CH_3}{\underset{|}{N}}}(CH_3){-}(CH_2)_3NHCONH(CH_2)_3\overset{\oplus}{\underset{CH_3}{\underset{|}{N}}}(CH_3){-}CH_2{-}C_6H_4{-}O{-}C_6H_4{-}CH_2{-} \right]$ 2Cl$^\ominus$ | 99.6 | 0.45 |
| (k) ClCH$_2$CH(OH)CH$_2$Cl | (110) $\left[ -\overset{\oplus}{\underset{CH_3}{\underset{|}{N}}}(CH_3)(CH_2)_3NHCONH(CH_2)_3\overset{\oplus}{\underset{CH_3}{\underset{|}{N}}}(CH_3)CH_2CH(OH)CH_2{-} \right]$ 2Cl$^\ominus$ | 86 | 0.21 |
| (l) ClCH$_2$O(CH$_2$)$_6$OCH$_2$Cl | (111) $\left[ -\overset{\oplus}{\underset{CH_3}{\underset{|}{N}}}(CH_3)(CH_2)_3NHCONH(CH_2)_3\overset{\oplus}{\underset{CH_3}{\underset{|}{N}}}(CH_3)CH_2O(CH_2)_6OCH_2{-} \right]$ 2Cl$^\ominus$ | 99 | 0.14 |

EXAMPLE 2

Example 1a is repeated using the following molar ratios:

| 4,4'-bis-(chloromethyl)-diphenyl/1,3-bis-(3-dimethyl-aminopropyl)-urea: | Content of ionic halogen in % of theory | Viscosity ($\mu$) |
|---|---|---|
| 1:0.97 | 98.5 | 1.42 |
| 1:0.94 | 98.2 | 0.83 |
| 1:0.90 | 97.4 | 0.22 |

The resulting water-soluble polymers have recurring units of the formula (101).

EXAMPLE 3

Equimolar amounts (0.2 mol in each case) of the diamines indicated in Table 2 and of 4,4'-bis-(chloromethyl)-diphenyl are reacted in accordance with Example 1. Reaction products containing the recurring units indicated in Table 2 are obtained in quantitative yield (100% of theory).

Table 2

| Diamine | Reaction product containing recurring units of the formula | Content of ionic halogen in % of theory | Viscosity ($\mu$) |
|---|---|---|---|
| CH$_3$-N(CH$_3$)-CH$_2$CH$_2$NHCONHCH$_2$CH$_2$-N(CH$_3$)-CH$_3$ | (112) $\left[ -\overset{\oplus}{\underset{CH_3}{\underset{|}{N}}}(CH_3)CH_2CH_2NHCONHCH_2CH_2\overset{\oplus}{\underset{CH_3}{\underset{|}{N}}}(CH_3){-}CH_2{-}C_6H_4{-}C_6H_4{-}CH_2{-} \right]$ 2Cl$^\ominus$ | 97.6 | 0.54 |
| C$_2$H$_5$-N(C$_2$H$_5$)-(CH$_2$)$_3$-NHCONH-(CH$_2$)$_3$-N(C$_2$H$_5$)-C$_2$H$_5$ | (113) $\left[ -\overset{\oplus}{\underset{C_2H_5}{\underset{|}{N}}}(C_2H_5)(CH_2)_3NHCONH(CH_2)_3\overset{\oplus}{\underset{C_2H_5}{\underset{|}{N}}}(C_2H_5){-}CH_2{-}C_6H_4{-}C_6H_4{-}CH_2{-} \right]$ 2Cl$^\ominus$ | 96.7 | 0.20 |
| piperidino—(CH$_2$)$_3$NHCONH(CH$_2$)$_3$—piperidino | (114) $\left[ -\overset{\oplus}{N}(piperidino)(CH_2)_3NHCONH(CH_2)_3\overset{\oplus}{N}(piperidino){-}CH_2{-}C_6H_4{-}C_6H_4{-}CH_2{-} \right]$ 2Cl$^\ominus$ | 97.2 | 0.34 |

EXAMPLE 4

Equimolar amounts (0.2 mol in each case) of the dihalides indicated in Table 3 and of 1,2-bis-(dimethylaminopropyl)-oxalamide (prepared from diethyl oxalate and 1-dimethylamino-3-aminopropane) were reacted in accordance with Example 1. Reaction products containing the recurring units indicated in Table 3 containing the recurring units indicated in Table 4 are obtained in quantitative yield (100% of theory).

Table 4

| Dihalide | | Reaction product containing recurring units of the formula | Content of ionic halogen in % of theory | Viscosity (μ) |
|---|---|---|---|---|
| ClCH$_2$-⟨⟩-⟨⟩-CH$_2$Cl | (120) | $\left[-\overset{\oplus}{\underset{CH_3}{\overset{CH_3}{N}}}-(CH_2)_3NHOC(CH_2)_4CONH(CH_2)_3\overset{\oplus}{\underset{CH_3}{\overset{CH_3}{N}}}-CH_2-⟨⟩-⟨⟩-CH_2-\right]2Cl^{\ominus}$ | 98 | 0.64 |
| ClCH$_2$-⟨⟩-CH$_2$Cl | (121) | $\left[-\overset{}{\underset{CH_3}{\overset{CH_3}{N}}}-(CH_2)_3NHCO(CH_2)_4CONH(CH_2)_3\overset{\oplus}{\underset{CH_3}{\overset{CH_3}{N}}}-CH_2-⟨⟩-CH_2-\right]2Cl^{\ominus}$ | 100 | 0.35 |
| Br(CH$_2$)$_6$Br | (122) | $\left[-\overset{}{\underset{CH_3}{\overset{CH_3}{N}}}(CH_2)_3NHCO(CH_2)_4CONH(CH_2)_3\overset{\oplus}{\underset{CH_3}{\overset{CH_3}{N}}}-(CH_2)_6-\right]2Br^{\ominus}$ | 98 | 0.31 | are obtained in quantitative yield (100% of theory).

Table 3

| Dihalide | | Reaction product containing recurring units of the formula | Content of ionic halogen in % of theory | Viscosity (μ) |
|---|---|---|---|---|
| (a) ClCH$_2$-⟨⟩-⟨⟩-CH$_2$Cl | (115) | $\left[-\overset{\oplus}{\underset{CH_3}{\overset{CH_3}{N}}}(CH_2)_3NHCOCONH(CH_2)_3\overset{\oplus}{\underset{CH_3}{\overset{CH_3}{N}}}CH_2-⟨⟩-⟨⟩-CH_2-\right]2Cl^{\ominus}$ | 98 | 1.2 |
| (b) ClCH$_2$-⟨⟩-CH$_2$Cl | (116) | $\left[-\overset{\oplus}{\underset{CH_3}{\overset{CH_3}{N}}}(CH_2)_3NHCOCONH(CH_2)_3\overset{\oplus}{\underset{CH_3}{\overset{CH_3}{N}}}CH_2-⟨⟩-CH_2-\right]2Cl^{\ominus}$ | 98 | 0.42 |
| (c) Br-⟨⟩-Br (ortho) | (117) | $\left[-\overset{\oplus}{\underset{CH_3}{\overset{CH_3}{N}}}(CH_2)_3NHCOCONH(CH_2)_3\overset{\oplus}{\underset{CH_3}{\overset{CH_3}{N}}}CH_2-⟨⟩-CH_2-\right]2Br^{\ominus}$ | 97.5 | 0.36 |
| (d) Br(CH$_2$)$_6$Br | (118) | $\left[-\overset{\oplus}{\underset{CH_3}{\overset{CH_3}{N}}}(CH_2)_3NHCOCONH(CH_2)_3\overset{\oplus}{\underset{CH_3}{\overset{CH_3}{N}}}(CH_2)_6-\right]2Br^{\ominus}$ | 97 | 0.46 |
| (e) Br(CH$_2$)$_{12}$Br | (119) | $\left[-\overset{\oplus}{\underset{CH_3}{\overset{CH_3}{N}}}(CH_2)_3NHCOCONH(CH_2)_3\overset{\oplus}{\underset{CH_3}{\overset{CH_3}{N}}}(CH_2)_{12}-\right]2Br^{\ominus}$ | 97 | 0.55 |

EXAMPLE 5

Equimolar amounts (0.2 mol in each case) of the dihalides indicated in Table 4 and of 1,6-bis-(3-dimethylaminopropyl)-adipamide (prepared from diethyl adipate and 1-dimethylamino-3-aminopropane) are reacted in accordance with Example 1. Reaction products

EXAMPLE 6

Equimolar amounts (0.2 mol in each case) of 1,6-dibromohexane and of the diamine of the formula

are reacted in accordance with Example 1. The reaction product containing recurring units of the formula

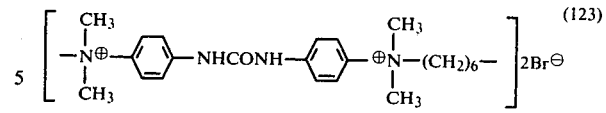

is obtained in quantitative yield (100% of theory).

The inherent viscosity $\mu$ (dl/g) is: 0.18.

The content of ionically bonded bromine is: 97% (of theory).

EXAMPLE 7

Equimolar amounts (0.2 mol in each case) of the diamines indicated in Table 5 and of 4,4'-bis-(chloromethyl)-diphenyl are reacted in accordance with Example 1. Reaction products containing the recurring units indicated in Table 5 are obtained in quantitative yield (100% of theory).

Table 5

| Diamine | Reaction product containing recurring units of the formula | Content of ionic halogen in % of theory | Viscosity (μ) |
|---|---|---|---|
| $(CH_3)_2NCH_2CONHCH_2CH_2CH_2N(CH_3)_2$ | (124) $\left[ \oplus-N(CH_3)_2-NCH_2CONH(CH_2)_3\oplus N(CH_3)_2-CH_2-\text{biphenyl}-CH_2- \right] 2Cl^\ominus$ | 97.5 | 0.65 |
| $(CH_3)_2N\text{-}C_6H_4\text{-}CONH(CH_2)_3N(CH_3)_2$ | (125) $\left[ \oplus-N(CH_3)_2-C_6H_4-CONH(CH_2)_3\oplus N(CH_3)_2-CH_2-\text{biphenyl}-CH_2- \right] 2Cl^\ominus$ | 97.2 | 0.12 |
| $(CH_3)_2N(CH_2)_3NHOC\text{-}C_6H_4\text{-}CONH(CH_2)_3N(CH_3)_2$ | (126) $\left[ \oplus-N(CH_3)_2-(CH_2)_3NHCO-C_6H_4-CONH(CH_2)_3\oplus N(CH_3)_2-CH_2-\text{biphenyl}-CH_2- \right] 2Cl^\ominus$ | 98 | 0.10 |
| $(CH_3)_2N(CH_2)_3NHOCNH(CH_2)_6NHCONH(CH_2)_3N(CH_3)_2$ | (127) $\left[ \oplus-N(CH_3)_2-(CH_2)_3NHOCNH(CH_2)_6NHCONH(CH_2)_3\oplus N(CH_3)_2-CH_2-\text{biphenyl}-CH_2- \right] 2Cl^\ominus$ | 97 | 0.39 |
| $(CH_3)_2N(CH_2)_3NHCONH\text{-}C_6H_3(CH_3)\text{-}NHCONH(CH_2)_3N(CH_3)_2$ | (128) $\left[ \oplus-N(CH_3)_2-(CH_2)_3NHCONH-C_6H_3(CH_3)-NHCONH(CH_2)_3\oplus N(CH_3)_2-CH_2-\text{biphenyl}-CH_2- \right] 2Cl^\ominus$ | 97.6 | 0.20 |
| $(CH_3)_2N(CH_2)_3OOC\text{-}C_6H_4\text{-}COO(CH_2)_3N(CH_3)_2$ | (129) $\left[ \oplus-N(CH_3)_2-(CH_2)_3OOC-C_6H_4-COO(CH_2)_3\oplus N(CH_3)_2-CH_2-\text{biphenyl}-CH_2- \right] 2Cl^\ominus$ | 97.3 | 0.31 |
| $(CH_3)_2N(CH_2)_3OOCNH(CH_2)_6NHCOO(CH_2)_3N(CH_3)_2$ | (130) $\left[ \oplus-N(CH_3)_2-(CH_2)_3OOCNH(CH_2)_6NHCOO(CH_2)_3\oplus N(CH_3)_2-CH_2-\text{biphenyl}-CH_2- \right] 2Cl^\ominus$ | 97.6 | 0.36 |
| $(CH_3)_2NCH_2CONH(CH_2)_3NHCOCH_2N(CH_3)_2$ | (131) $\left[ \oplus-N(CH_3)_2-NCH_2CONH(CH_2)_3NHCOCH_2\oplus N(CH_3)_2-CH_2-\text{biphenyl}-CH_2- \right] 2Cl^\ominus$ | 98.2 | 0.32 |

EXAMPLE 8

Mixtures of dihalides and diamines (equimolar amounts of the dihalides and diamines) are reacted in accordance with the procedure of Example 1a. Reaction products of the composition indicated in Table 6 are obtained in quantitative yield (100% of theory):

Dihalides and diamines used:

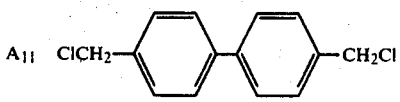

$A_{12}$ $BrCH_2CH_2CH_2CH_2CH_2CH_2Br$
$B_1$ $(CH_3)_2NCH_2CH_2N(CH_3)_2$
$B_2$ $(CH_3)_2NCH_2CH_2CH_2N(CH_3)_2$
$B_3$ $(CH_3)_2NCH_2CH_2CH_2CH_2CH_2N(CH_3)_2$
$B_4$ $(CH_3)_2NC_3H_6NHCONHC_3H_6N(CH_3)_2$
$B_5$ $(CH_3)_2NC_3H_6NHCOCONHC_3H_6N(CH_3)_2$

Table 6

| Polymeric quaternary reaction products prepared from (mols) | Content of ionic halogen in % of theory | Viscosity ($\mu$) |
|---|---|---|
| (132) (1)$A_{11}$ + ($\frac{1}{2}$)$B_1$ + ($\frac{1}{2}$)$B_4$ | 97.1 | 0.27 |
| (133) (1)$A_{11}$ + ($\frac{1}{2}$)$B_2$ + ($\frac{1}{2}$)$B_4$ | 98.3 | 0.28 |
| (134) (1)$A_{11}$ + ($\frac{1}{2}$)$B_3$ + ($\frac{1}{2}$)$B_4$ | 99.7 | 0.30 |
| (135) ($\frac{1}{2}$)$A_{11}$ + ($\frac{1}{2}$)$A_{12}$ + (1)$B_4$ | 97.9 | 0.29 |
| (136) ($\frac{1}{2}$)$A_{11}$ + ($\frac{1}{2}$)$A_{12}$ + (1)$B_5$ | 98 | 0.27 |
| (137) ($\frac{1}{2}$)$A_{11}$ + ($\frac{1}{2}$)$A_{12}$ + ($\frac{1}{2}$)$B_4$ + ($\frac{1}{2}$)$B_2$ | 99.5 | 0.28 |
| (138) ($\frac{1}{2}$)$A_{11}$ + ($\frac{1}{2}$)$A_{12}$ + ($\frac{1}{2}$)$B_5$ + ($\frac{1}{2}$)$B_2$ | 98.1 | 0.17 |

EXAMPLE 9

5 g of a fabric made of polyacrylonitrile (Orlon 42 - Du Pont) are treated for 20 minutes at 98° C. in a dyeing apparatus in 200 ml of a liquor which contains 0.01 g of the reaction product containing the recurring units of the formula (101) (assistant) and the pH of which has been adjusted to 4 with 80% strength acetic acid, the fabric being agitated continuously during the treatment. The following mixture of dyes, consisting of 0.007 g of the dye of the formula (139)

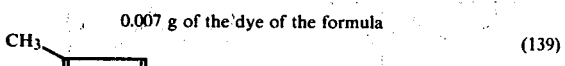

0.007 g of the dye of the formula (140)

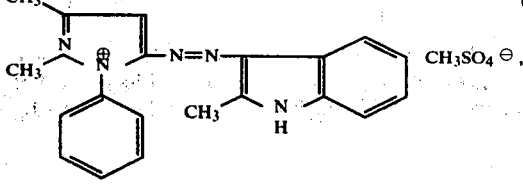

0.01 g of the dye of the formula (141)

is then added to the liquor, the temperature being kept at 98° C. Dyeing is then carried out for 60 minutes at this temperature, the liquor is cooled slowly to 60° C. and the fabric is rinsed and dried.

A slow, constant-shade build-up of the colour shade on the fibre is achieved by the addition of the assistant (retarder). The customary cooling after preshrinking is no longer necessary.

The resulting grey dyeing is distinguished by outstanding levelness and good penetration and by good wet fastness properties.

Similarly good results are obtained when the assistant used is 0.1 g of the other reaction products described in Examples 1 to 8.

EXAMPLE 10

A polyester fabric is impregnated with a liquor which contains 15 g/l of the polymeric quaternary ammonium salt containing the recurring units of the formula (101), then squeezed off to an increase in weight of 110% and dried for 30 minutes at 80° C. The fabric is then thermofixed for 30 seconds at 170° C.

The surface resistance of the fabric is measured, and the following values were determined.

Untreated polyester: $4 \times 10^{13}$ ohms
Treated polyester: $1 \times 10^9$ ohms

EXAMPLE 11

An industrial effluent which contains about 100 ppm of a mixture of reactive dyes and acid dyes is mixed, as it runs into the settling basin of a sewage treatment plant, with a solution of the assistant according to Example (1a) in such a way that a total of 100 ppm of the assistant is introduced into the solution. Spontaneous precipitation of the dye takes place. The precipitated dye can be separated off by filtration after only 30 minutes and the remaining effluent (filtrate) can be fed as a completely decolorised liquid into the drainage system.

As a rule, however, it is not customary to filter but rather to allow the precipitates to sediment.

In the present case, the precipitated dye settles on the bottom in about 5 to 6 hours and the completely decolorised supernatant water can be pumped into the drainage system.

What is claimed is:

1. A polymeric quaternary ammonium salt which contains recurring units of the formula $$\left[ \begin{array}{c} R_1 \\ | \\ -N^{\oplus}-A_1-X-A_2-N^{\oplus}-A_3- \\ | \\ R_2 \end{array} \begin{array}{c} R_3 \\ | \\ \\ | \\ R_4 \end{array} \right] 2Q^{\ominus}$$

alone, or in combination with units of the formula $$\left[ \begin{array}{c} R_1 \\ | \\ -N^{\oplus}-A_1'-N^{\oplus}-A_3- \\ | \\ R_2 \end{array} \begin{array}{c} R_3 \\ | \\ \\ | \\ R_4 \end{array} \right] 2Q^{\ominus}$$

wherein $R_1$, $R_2$, $R_3$ and $R_4$ are identical or different and are alkyl, hydroxyalkyl, cyanoalkyl, alkoxyalkyl, alkylthioalkyl or alkylcarbonylalkyl having 1 to 10 carbon atoms; alkylsulphonylalkyl having 1 to 4 carbon atoms in the alkyl moiety; alkylcarboxylic acid having 1 to 4 carbon atoms in the alkyl moiety; carbalkoxyalkyl and di-(carbalkoxy)-alkyl each having 1 to 4 carbon atoms in the alkoxy moiety and in the alkyl moiety; carboxylic acid amide-alkyl which has 1 to 10 carbon atoms in the alkyl moiety and is unsubstituted or N-substituted by lower alkyl; cycloalkyl or alkenyl having at most 20 carbon atoms; or phenyl or benzyl, which are unsubstituted by hydroxyl, cyano, fluoro, chloro, bromo, alkyl, hydroxyalkyl, cyanoalkyl, alkoxy or alkylthio having 1 or 2 carbon atoms;

$A_1$ and $A_2$ are $-C_nH_{2n}-$, in which n is 1 to 12, and the sum of n in $A_1$ and $A_2$ is at least 3, and when n is 1 the bond to the bridge member X is not via a nitrogen or oxygen atom; or are phenylene; and $A_1$ and $A_2$ are identical or different from one another;

$A_1'$ is $-C_iH_{2i}-$ in which i is 2 to 12;

$A_3$ is $-C_mH_{2m}-$, $-CH_2O-R_5OOCCH_2-$, $-CH_2(OR_6)_pOCH_2-$, $-CH_2COCH_2-$,

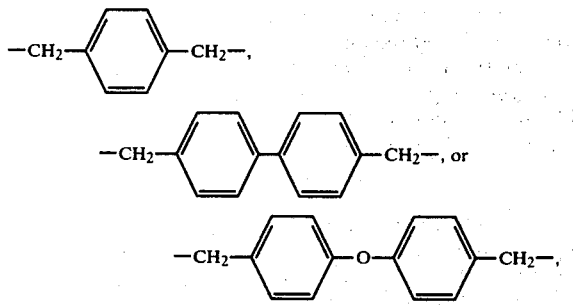

in which $R_5$ is straight-chain or branched alkylene having 2 to 12 carbon atoms, which is unsubstituted or substituted by halogen, $R_6$ is $-CH_2CH_2-$, $-CH_2CH(CH_3)-$, or $-(CH_2)_4-$, m is 2 to 12 and p is 2 to 15;

X is a divalent bridge member of the formula $-NHCONH-$; $-NHCOX_1CONH-$; $-CONH-$; $-OCONH-$; $-COO-$; $-COX_2CO-$;

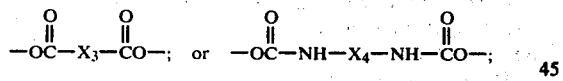

in which $X_1$ is a direct bond, alkylene, alkylene, arylene, diaminoalkylene, diaminoarylene, dioxyalkylene, polyoxyalkylene, or dioxyarylene, $X_2$ is a direct bond, diaminoalkylene, dioxyalkylene, polyoxyalkylene or dithioalkylene, $X_3$ is arylene and $X_4$ is alkylene or arylene, and Q is halo, sulphate, methyl sulphate, ethyl sulphate, toluene sulphonate or nitrate.

2. A polymeric quaternary ammonium salt according to claim 1, wherein the recurring units are of the formula

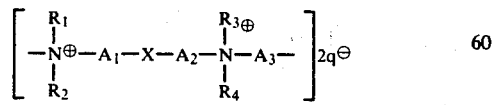

3. A polymeric quaternary ammonium salt according to claim 2, wherein X is $-NHCONH-$, $-NHCOX_1CONH-$, $-CONH-$, $-OCONH-$, $-COO-$ or $-COX_2CO-$, $X_1$ is alkylene, alkenylene, arylene, diaminoalkylene, diaminoarylene, dioxyalkylene, poly- oxyalkylene or dioxyarylene and $X_2$ is diaminoalkylene, dioxyalkylene, polyoxyalkylene or dithioalkylene.

4. A polymeric quaternary ammonium salt according to claim 3, wherein the recurring units are of the formula

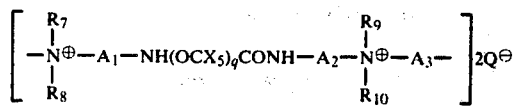

wherein $R_7$, $R_8$, $R_9$ and $R^{10}$ are identical or different from one another and are cycloalkyl having 5 to 6 carbon atoms; alkyl, hydroxyalkyl, cyanoalkyl, alkoxyalkyl, alkylthioalkyl, or alkylcarbonylalkyl having 1 to 10 carbon atoms; alkylsulfonylalkyl having 1 to 4 carbon atoms in the alkyl moiety, alkylcarboxylic acid having 1 to 4 carbon atoms in the alkyl moiety; carbalkoxyalkyl or di-(carbalkoxy)-alkyl each having 1 to 4 carbon atoms in the alkoxy moiety and in the alkyl moiety; carboxylic acid amide-alkyl which has 1 to 10 carbon atoms in the alkyl moiety and is unsubstituted or N-substituted by lower alkyl;

$X_5$ is $-C_rH_{2r}-$ in which r is an integer from 1 to 12; $-(CH=CH)_s$, in which s is 1 or 2;

$-\underset{\underset{CH_3}{|}}{C}=CH-$; $CH_2=CCH_2-$; a radical of the formula

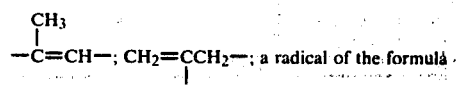

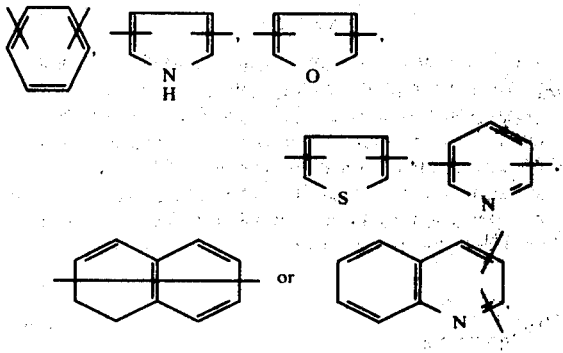

in which the aromatic rings thereof are unsubstituted or substituted by one or more of halo, alkyl or alkoxy; $-NH(CH_2)_mNH-$, in which m is 2 to 12;

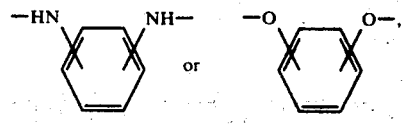

in which the phenylene rings thereof are unsubstituted or substituted by one or more of halo, alkyl or alkoxy;

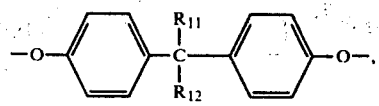

in which $R_{11}$ and $R_{12}$ are hydrogen or methyl; —$OR_5O$—; or —$(OR_6)_pO$—; and q is 0 or 1.

5. A polymeric quaternary ammonium salt according to claim 4, wherein $X_5$ is a direct chemical bond and q is 1.

6. A polymeric quaternary ammonium salt according to claim 5, wherein the recurring units are of the formula

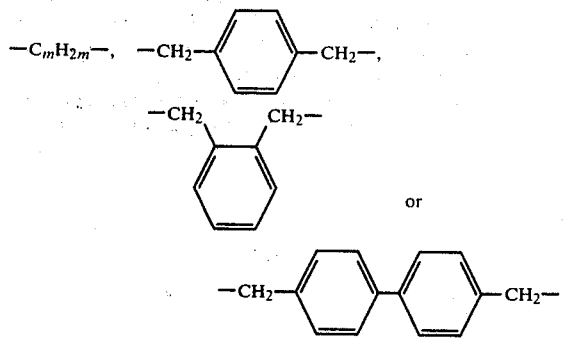

in which $R_{17}$ is alkyl of 1 to 4 carbon atoms, $A_7$ is

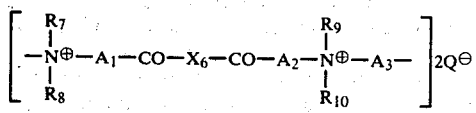

m is 2 to 12 and $m_1$, is 2 to 6.

7. A polymeric quaternary ammonium salt according to claim 2, wherein the recurring units are of the formula

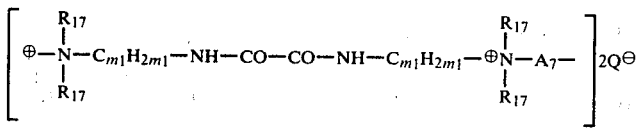

wherein
$R_7$, $R_8$, $R_9$ and $R_{10}$ are identical or different from one another and are cycloalkyl having 5 to 6 carbon atoms; alkyl, hydroxyalkyl, cyanoalkyl, alkoxyalkyl, alkylthioalkyl, or alkylcarbonylalkyl having 1 to 10 carbon atoms; alkylsulfonylalkyl having 1 to 4 carbon atoms in the alkyl moiety; alkylcarboxylic acid having 1 to 4 carbon atoms in the alkyl moiety; carbalkoxyalkyl of di-(carbalkoxy)-alkyl each having 1 to 4 carbon atoms in the alkoxy moiety and in the alkyl moiety; carboxylic acid amide-alkyl which has 1 to 10 carbon atoms in the alkyl moiety and is unsubstituted or N-substituted by lower alkyl;

$X_6$ is —$OR_5O$—, —$(OR_6)_pO$—, —$S(CH_2)_mS$— or —$NH(CH_2)_mNH$—, where m is 2 to 12.

8. A polymeric quaternary ammonium salt according to claim 6, wherein the recurring units are of the formula

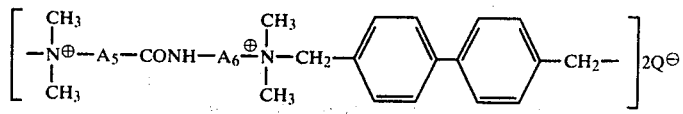

wherein
$A_5$ is alkylene having 1 to 4 carbon atoms or phenylene; and
$A_6$ is alkylene having 2 to 6 carbon atoms or phenylene.

9. A polymeric quaternary ammonium salt according to claim 2, wherein the recurring units are of the formula

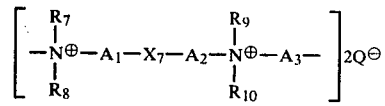

in which $X_7$ is

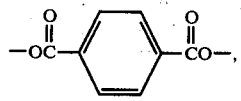

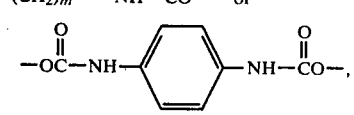

where m is 2 to 12; and
$R_7$, $R_8$, $R_9$ and $R_{10}$ are identical or different from one another and are cycloalkyl having 5 to 6 carbon atoms; alkyl, hydroxyalkyl, cyanoalkyl, alkoxyalkyl, alkylthioalkyl, or alkylcarbonylalkyl having 1 to 10 carbon atoms; alkylsulfonylalkyl having 1 to 4 carbon atoms in the alkyl moiety; alkylcarboxylic acid having 1 to 4 carbon atoms in the alkyl moiety; carbalkoxyalkyl or di-(carbalkoxy)-alkyl each having 1 to 4 carbon atoms in the alkoxy moiety and in the alkyl moiety; carboxylic acid amide-alkyl which has 1 to 10 carbon atoms in the alkyl moiety and is unsubstituted or N-substituted by lower alkyl.

10. A polymeric quaternary ammonium salt according to claim 4, having recurring units of the formula

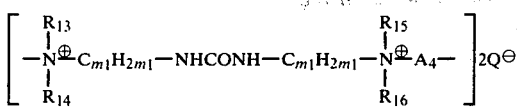

wherein

R$_{13}$, R$_{14}$, R$_{15}$ and R$_{16}$ are identical or different from one another and are alkyl, hydroxyalkyl, alkoxyalkyl, alkylthioalkyl or cyanoalkyl having 1 to 4 carbon atoms; cyclopentyl, cyclohexyl, CH$_3$COCH$_2$— or H$_2$NCOCH$_2$—; phenyl or benzyl which are unsubstituted or substituted by hydroxyl, cyano, fluoro, chloro, bromo, alkyl, hydroxyalkyl, cyanoalkyl, alkoxy or alkylthio having 1 to 2 carbon atoms; carbalkoxyalkyl or di-(carbalkoxy)-alkyl each having 1 or 2 carbon atoms in the alkyl moiety and in the alkoxy moiety; or —CH$_2$COOH, —(CH$_2$)$_2$COOH or carboxylic acid amide-alkyl which has 1 or 2 carbon atoms in the alkyl moiety and is N-substituted by lower akyl;

A$_4$ is —C$_m$H$_{2m}$—, —CH$_2$COCH$_2$—, —CH$_2$CHOH CH$_2$—,

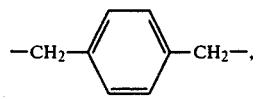

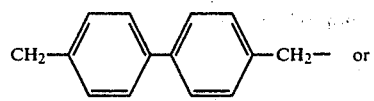

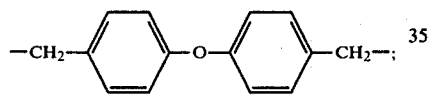

m is 2 to 12; and
m$_1$ is 2 to 6.

11. A polymeric quaternary ammonium salt according to claim 10, wherein R$_{13}$, R$_{14}$, R$_{15}$ and R$_{16}$ are identical or different from one another and are alkyl having 1 to 4 carbon atoms.

12. A polymeric quaternary ammonium salt according to claim 10, wherein R$_{13}$, R$_{14}$, R$_{15}$ and R$_{16}$ are methyl.

13. A polymeric quaternary ammonium salt according to claim 1, wherein R$_1$, R$_2$, R$_3$ and R$_4$ are identical or different from one another and are methyl or ethyl; A$_1$ and A$_2$ are —(CH$_2$)$_{n1}$— in which n$_1$ is 1 to 3 and the sum of n$_1$ in A$_1$ and A$_2$ is at least 3, or are phenylene; A$_3$ is —C$_m$H$_{2m}$—, —CH$_2$O(CH$_2$)$_{n2}$OCH$_2$—, —CH$_2$COCH$_2$— —CH$_2$CHOHCH$_2$—,

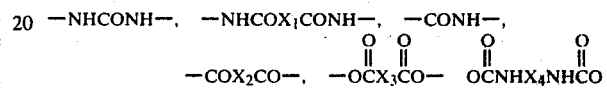

where m is 2 to 12 and n$_2$ is 2 to 6; and

X is a divalent bridge member of the formula

—NHCONH—, —NHCOX$_1$CONH—, —CONH—,

—COX$_2$CO—, —OCX$_3$CO— OCNHX$_4$NHCO
(with O=C double bonds as shown)

or where X$_1$ is a direct bond, alkylene having 1 to 6 carbon atoms, phenylene, diaminoalkylene having 1 to 6 carbon atoms or diaminophenylene and the phenylene ring is unsubstituted or substituted by methyl, X$_2$ is —NH(CH$_2$)$_{n2}$NH— where n$_2$ is 2 to 6 X$_3$ is phenylene and X$_4$ is alkylene having 2 to 6 carbon atoms or phenylene.

14. A polymeric quaternary ammonium salt according to claim 2, wherein the recurring units are of the formula

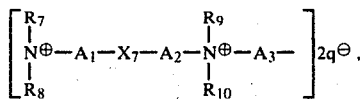

wherein

X$_7$ is —CONH, —OCONH— or —COO—;

R$_7$, R$_8$, R$_9$ and R$_{10}$ are identical or different from one another and are cycloalkyl having 5 to 6 carbon atoms; alkyl, hydroxyalkyl, cyanoalkyl, alkoxyalkyl, alkylthioalkyl, or alkylcarbonylalkyl having 1 to 10 carbon atoms; alkylsulfonylalkyl having 1 to 4 carbon atoms in the alkyl moiety; alkylcarboxylic acid having 1 to 4 carbon atoms in the alkyl moiety; carbalkoxyalkyl or di-(carbalkoxy)-alkyl each having 1 to 4 carbon atoms in the alkoxy moiety and in the alkyl moiety; carboxylic acid amide-alkyl which has 1 to 10 carbon atoms in the alkyl moiety and is unsubstituted or N-substituted by lower alkyl.

15. A polymeric quaternary ammonium salt according to claim 12, wherein the cationic units are of the formula

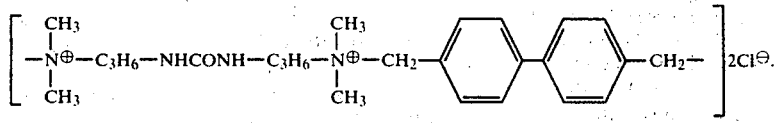

* * * * *

UNITED STATES PATENT AND TRADEMARK OFFICE
CERTIFICATE OF CORRECTION

PATENT NO. : 4,247,476
DATED : JANUARY 27, 1981
INVENTOR(S) : JAROSLAV HAASE ET AL

It is certified that error appears in the above-identified patent and that said Letters Patent are hereby corrected as shown below:

Claim 1, Column 27, lines 18 and 19 read:

"$A_3$ is $-C_mH_{2m}$, $-CH_2O-R_5OOCH_2-$, $-CH_2(OR_6)_pOCH_2-$, $-CH_2COCH_2-$,"

Should read:

-- $A_3$ is $-C_mH_{2m}$, $-CH_2O-R_5OOCH_2-$, $-CH_2(OR_6)_pOCH_2-$, $-CH_2COCH_2-$, $-CH_2CHOHCH_2-$, --

Signed and Sealed this

Sixteenth Day of February 1982

[SEAL]

Attest:

Attesting Officer

GERALD J. MOSSINGHOFF
Commissioner of Patents and Trademarks